US012594102B2

(12) United States Patent
Dharan

(10) Patent No.: US 12,594,102 B2
(45) Date of Patent: Apr. 7, 2026

(54) SURGICAL SUTURE ASSEMBLY

(71) Applicant: Murali Dharan, Danville, CA (US)

(72) Inventor: Murali Dharan, Danville, CA (US)

( * ) Notice: Subject to any disclaimer, the term of this patent is extended or adjusted under 35 U.S.C. 154(b) by 277 days.

(21) Appl. No.: 16/035,559

(22) Filed: Jul. 13, 2018

(65) Prior Publication Data

US 2019/0133654 A1 May 9, 2019

Related U.S. Application Data

(60) Provisional application No. 62/532,092, filed on Jul. 13, 2017.

(51) Int. Cl.
*A61B 17/82* (2006.01)
*A61B 17/06* (2006.01)
*A61B 17/84* (2006.01)
*A61B 17/88* (2006.01)
*A61B 90/00* (2016.01)

(52) U.S. Cl.
CPC ............ *A61B 17/823* (2013.01); *A61B 17/06* (2013.01); *A61B 17/06166* (2013.01); *A61B 17/842* (2013.01); *A61B 17/8861* (2013.01); *A61B 90/08* (2016.02); *A61B 2017/06028* (2013.01); *A61B 2090/0807* (2016.02)

(58) Field of Classification Search
CPC ... A61B 17/82; A61B 17/823; A61B 17/8861; A61B 17/06166
See application file for complete search history.

(56) References Cited

U.S. PATENT DOCUMENTS

| | | | | |
|---|---|---|---|---|
| 3,322,125 A | * | 5/1967 | Kurtz ................... | A61L 17/145 427/430.1 |
| 3,926,194 A | * | 12/1975 | Greenberg ....... | A61B 17/06004 223/102 |
| 5,127,413 A | * | 7/1992 | Ebert ..................... | A61B 17/06 606/103 |
| 5,643,295 A | * | 7/1997 | Yoon .................. | A61B 17/0469 606/232 |
| 5,645,568 A | * | 7/1997 | Chervitz .......... | A61B 17/06166 606/228 |
| 6,015,428 A | * | 1/2000 | Pagedas ............. | A61B 17/0483 606/232 |
| 6,607,541 B1 | * | 8/2003 | Gardiner ................ | A61B 17/06 606/232 |
| 7,329,271 B2 | * | 2/2008 | Koyfman ......... | A61B 17/06166 606/228 |
| 7,481,826 B2 | * | 1/2009 | Cichocki, Jr. .... | A61B 17/06066 604/148 |
| 7,547,313 B2 | * | 6/2009 | Gardiner .............. | A61B 17/064 606/151 |
| 8,709,023 B2 | * | 4/2014 | Shalaby ................ | A61L 17/145 606/151 |

(Continued)

FOREIGN PATENT DOCUMENTS

| | | | | | |
|---|---|---|---|---|---|
| EP | | 3653135 A1 | * | 5/2020 | ............. A61B 17/06 |
| WO | WO-2007025241 A2 | | * | 3/2007 | ....... A61B 17/06166 |

*Primary Examiner* — Anu Ramana

(74) *Attorney, Agent, or Firm* — Ross M. Carothers

(57) ABSTRACT

Surgical suture assemblies, and methods of their use, are disclosed having configurations suitable for closure of biological tissue, including the bony tissue of the sternum. The surgical suture assemblies described or contemplated herein have physical characteristics that help to mitigate undesirable issues, such as bleeding.

22 Claims, 10 Drawing Sheets

(56)              References Cited

U.S. PATENT DOCUMENTS

| | | | |
|---|---|---|---|
| 11,110,197 B2 * | 9/2021 | Xia ........................ | A61L 17/005 |
| 2002/0077631 A1 * | 6/2002 | Lubbers ................ | A61F 2/0811 |
| | | | 606/232 |
| 2006/0161160 A1 * | 7/2006 | Sander ................... | A61B 17/06 |
| | | | 606/232 |
| 2007/0179529 A1 * | 8/2007 | Doyle ............. | A61B 17/06166 |
| | | | 606/228 |
| 2010/0274283 A1 * | 10/2010 | Kirsch ............... | A61B 17/0401 |
| | | | 606/228 |
| 2011/0264138 A1 * | 10/2011 | Avelar ................... | A61B 90/94 |
| | | | 606/228 |

* cited by examiner

SURGICAL SUTURE ASSEMBLY

This application claims the benefit of priority from U.S. Provisional Application Ser. No. 62/532,092, entitled "Surgical Suture Assembly," filed Jul. 13, 2017, the entire contents of which is incorporated herein by reference.

BACKGROUND

Field of this Disclosure

This disclosure relates generally to medical devices, and more particularly, to medical suture assemblies used to close incisions in biological tissue during medical procedures, including sternotomy procedures.

DESCRIPTION OF THE RELATED ART

Thoracic surgery to treat diseased or injured organs in the thorax has become very common. Currently, 300,000 to 400,000 open heart surgeries are performed annually in the U.S., and as many as 700,000 worldwide. Thoracic surgery, such as open heart surgery, conventionally requires a sternotomy to allow the surgeon to gain access to the thorax. Typically, such procedures require a sternotomy and upon completion of the procedure, the sternum would be closed using a wire suture.

In particular, with reference to FIGS. 1 and 2, a sternum 10, depicted in part, may be split or cut into two portions during a sternotomy procedure. After the median sternotomy, the sternum is divided into a first portion or first hemisternum 12 and a second portion or second hemisternum 14, to provide access to the thoracic cavity. After performance of a medical procedure the sternum 10 portions 12, 14 may be aligned and held together with a plurality of wire loops 20. Each of the wire loops 20 may be advance through a corresponding sternum 10 portion 12, 14 using a needle or sharpened tip, the needle creating corresponding openings 16 through the associated portion 12, 14. The wire loops 20 may originate as suture wire attached to a proximal end of the needle portion, for example. While the sternum 10 of FIG. 1 generally depicts the main body of the sternum for illustration purposes, one or more of the wires 20 may be advanced through one or more of the manubrium, xiphoid process, or parasternal tissue. This is also true for the various surgical suture assembly embodiments disclosed or contemplated herein.

Turning to FIGS. 3A and 3B, a suture assembly 100 known in the art is depicted. As shown, the needle assembly includes a needle 110 portion and a wire 120 portion. The needle 110 includes a sharpened tip 112, a body 114, and a proximal end 116, which is coupled to a distal end 222 of the wire 120. The needle 10 may be curved, as depicted, the curved portion having a radius R. With specific reference to FIG. 3B, at the proximal end 116, the needle has a diameter 116D and the distal end 122 of the wire 120 has a diameter 122D. As shown, the diameter 116D of the needle is generally larger than the diameter 122D of the distal end 122 of the wire 120. This difference in diameter results in openings 16 in biological tissue, such as bony tissue, created by the needle 110 having diameters greater than the diameter of the associated wire 120 surgical suture. Such differences in diameters may result in undesirable bleeding requiring further treatment.

Turning back to FIGS. 1 and 2, after the needle 110 is advanced through both sternum 10 portions 12, 14, the needle portion can be removed and the wire ends may be twisted, as generally depicted, to provide adequate pressure between the sternum 10 portions 12, 14. With specific reference to FIG. 2, the twisting of the wire 20 may act to further enlarge the openings 16 originally created by the needle 110, possibly leading to further undesirable bleeding.

Accordingly, there is a need for a surgical suture assembly intended for closing biological tissues, such as the bony tissue of the sternum, which are configured to mitigate bleeding while providing adequate closure pressure. There is a further need to provide a surgical suture assembly which allows users to more easily manipulate and use, leading to safer procedures taking less time.

BRIEF SUMMARY

Consistent with the present disclosure, a surgical suture assembly may include a needle portion having a diameter and a wire portion having a diameter, the diameter of the wire portion being greater than the diameter of the needle portion. In some embodiments, a suture assembly may comprise a first elongate member or portion having a diameter, a tapered distal portion ending in a distal tip, and a proximal end, and a second elongate member or portion have a distal end, a first diameter at a first location and a second diameter at a second location, the distal end of the second elongate member being coupled to the proximal end of the first elongate portion, the first location being distal to the second location, and the second diameter of the second elongate member being greater than the diameter of the first elongate member. The first diameter of the second elongate member may be less than the second diameter of the second elongate member, and the first diameter of the second elongate member may be less than the diameter of the first elongate member.

In some embodiments, the distal tip of the first elongate member may include a sharpened tip. In certain embodiments, the first elongate member is substantially straight and in other embodiments the first elongate member may include a curved portion. In some embodiments, the ratio of the second diameter of the second elongate member to the first diameter of the second elongate member is in a range from about 1 to about 3.

In still some embodiments, the second elongate member includes one or a plurality of monofilaments. In some embodiments, each of the plurality of monofilaments may have the same diameter, while in other embodiments, one or more of the plurality of monofilaments may have a diameter different from a diameter of the remaining ones of the plurality of monofilaments. In certain embodiments, each of the plurality of monofilaments may have a diameter which is different than the remaining ones of the plurality of monofilaments, while in other embodiments a first group of the plurality of monofilaments may have a diameter that is different than a diameter of a second group of the plurality of monofilaments. In still other embodiments, there may be a first number of the plurality of monofilaments at a first distance from a proximal end of the first elongate member, and a second number of the plurality of monofilaments at a second distance from a proximal end of the first elongate member. In other embodiments, there may be a first number of the plurality of monofilaments at the first location of the second elongate member and a second number of the plurality of monofilaments at the second location of the second elongate member.

In another aspect, a method includes providing a surgical suture assembly having a needle portion including a diameter and a wire portion including a diameter, the diameter of the wire portion being greater than the diameter of the needle portion, advancing the needle portion through biological tissue, and advancing the wire portion into the biological tissue. In certain embodiments, the biological tissue is bony tissue, such as the sternum. In certain embodiments advancing the needle portion through biological tissue includes advancing the needle portion through a first portion of the sternum and advancing the needle portion through a second portion of the sternum. In certain embodiments, advancing the wire portion into the biological tissue includes advancing the wire portion through the first and second portions of the sternum.

BRIEF DESCRIPTION OF THE DRAWINGS

Reference will be made to embodiments of the disclosure, examples of which may be illustrated in the accompanying figures. These figures are intended to be illustrative, not limiting. Although certain aspects of the embodiments are generally described in the context of these embodiments, it should be understood that such description is not intended to limit the scope to these particular embodiments. In the drawings.

DETAILED DESCRIPTION

Surgical suture assemblies, and methods of their use, are disclosed having configurations suitable for closing biological tissue, in particular, bony tissue. Surgical suture assemblies described or contemplated herein include certain physical characteristics to mitigate bleeding, while providing other physical characteristics to allow for easier handling and placement during use.

The following description is set forth for explanation to provide an understanding of the various embodiments of the present disclosure. However, as should be apparent, one skilled in the art will recognize that embodiments of the present disclosure may be incorporated into numerous other assemblies, systems and devices.

The embodiments of the present disclosure may include certain aspects each of which may be present in one or more medical devices, assemblies, or systems thereof. Assemblies and devices shown below are not necessarily to scale and are illustrative of exemplary embodiments. Furthermore, the illustrated exemplary embodiments disclosed herein may include more or less structures than depicted, and are not intended to be limited to the specific depicted structures. While various portions of the present disclosure are described relative to specific structures or processes with respect to a medical device, assembly, or system using specific labels these labels are not meant to be limiting.

The surgical suture assemblies described herein may be made from any suitable biocompatible material, including but not limited to metals, metal alloys (e.g. stainless steel) and polymers (e.g. polycarbonate), and may be formed using any appropriate process, such as extrusion or milling, screw-machining or molding (e.g. injection molding). Furthermore, the surgical suture assemblies described or contemplated herein may have any suitable length, extending from a distal tip of the needle portion to a proximal end of the suture wire, for the closure of biological tissue, the bony biological tissue of the sternum, for example. For illustration purposes only, such suitable lengths may be in the range from about 5 inches to about 20 inches.

Reference will now be made in detail to the present exemplary embodiments, which are illustrated in the accompanying drawings.

Figures 1, 2:
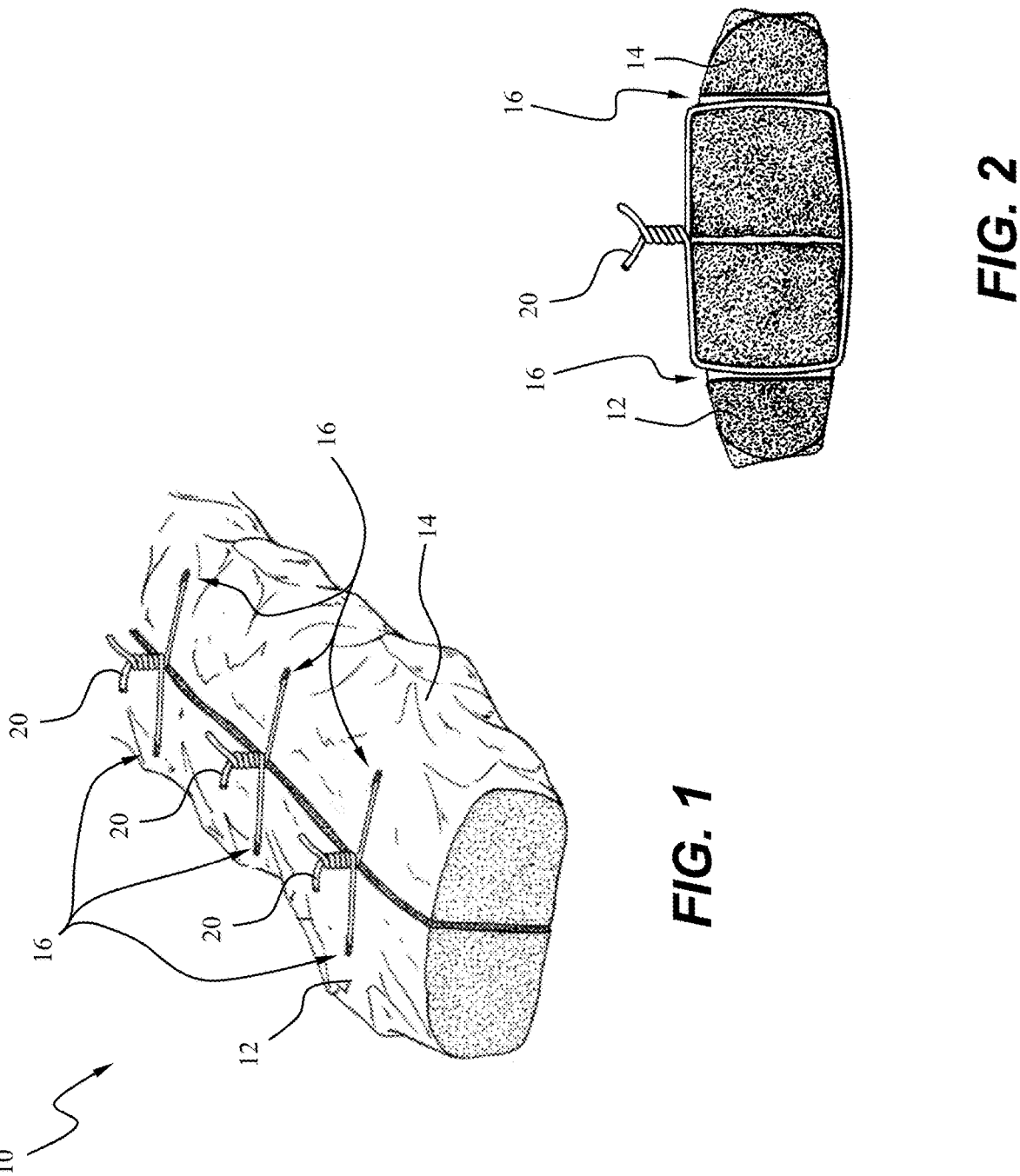
FIG. 1 depicts a perspective view of a partial sternum closed utilizing a known assembly, including multiple wire loops.
FIG. 2 depicts a section view of the partial sternum of FIG. 1, and one of the multiple wire loops.
Figure 3A:
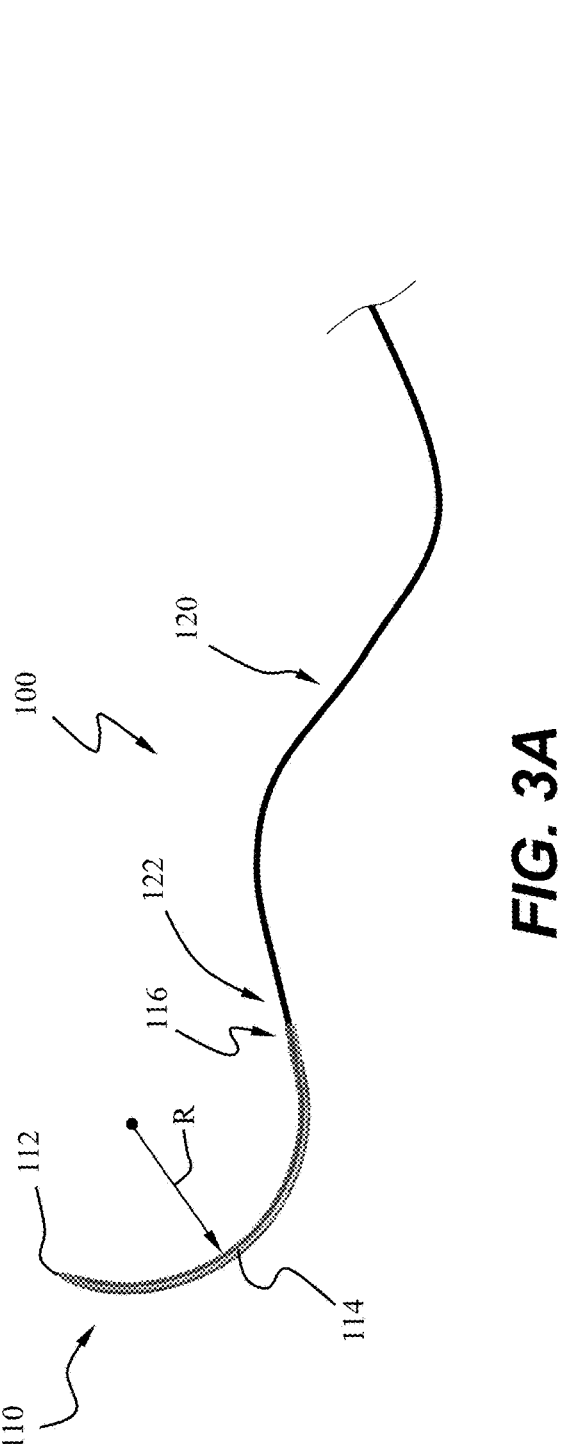
FIG. 3A is a partial view of a known suture assembly.
Figure 3B:
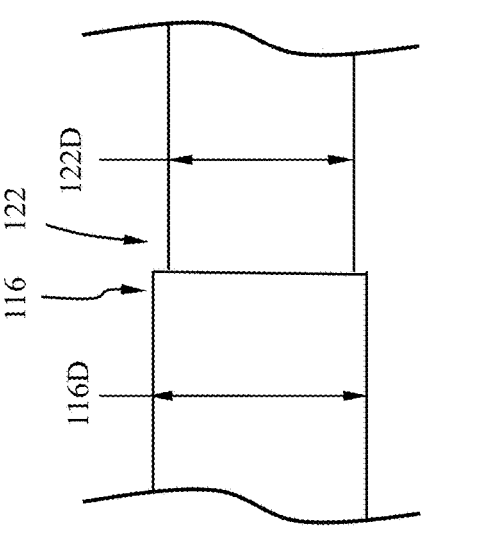
FIG. 3B is a more detailed depiction of a portion of the known suture assembly of FIG. 3A.
Figure 4:
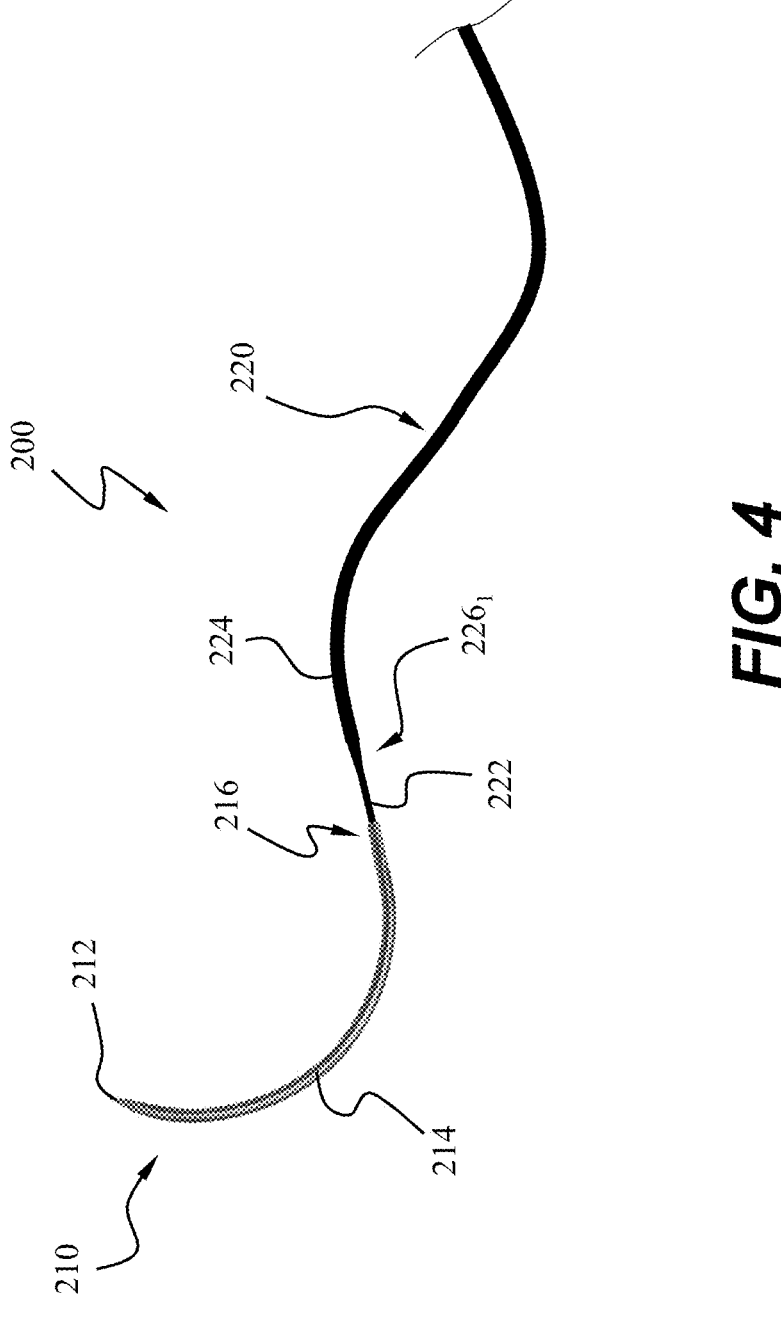
FIG. 4 is an exemplary suture assembly, in accordance with this disclosure.

Turning to FIG. 4, a surgical suture assembly 200 in accordance with this disclosure includes a first elongated member or needle portion 210 and a second elongate member or wire portion 220. The needle portion 210 may include a distal tip 212, which may be tapered to a point, a body portion 214 and a proximal portion 216 coupled to a distal portion 222 of the wire portion 220. The coupling between the needle portion 210 and the wire portion 220 may be through any suitable means including, for example, biocompatible adhesives, crimping, welding, or the like. For illustration purposes, the distal end 222 of the wire portion 220 may be inserted into a central opening (not shown) at the proximal portion 216 of the needle portion 210. Once inserted, the distal portion 216 may then be crimped to couple the needle portion 210 to the wire portion 220.

As shown, the wire portion 220 may include a first transition $226_1$ and a second transition $226_2$. The wire portions distal to the first transition $226_1$ and proximal to the second transition $226_2$ includes a first overall diameter, and wire portion 224 includes a second overall diameter, where the second overall diameter is greater than the first diameter, and greater than a diameter of the body 214 of needle portion 210. For illustration purposes only, the needle portion 214 may have a diameter of 4 mm, while the wire portion 224 may have a diameter of 5 mm. Accordingly, as the wire portion 224 passes through an opening in biological tissue created by the needle portion 210, wire portion 224 conforms to the biological tissue about the opening, helping to reduce bleeding, for example.

Figure 5:
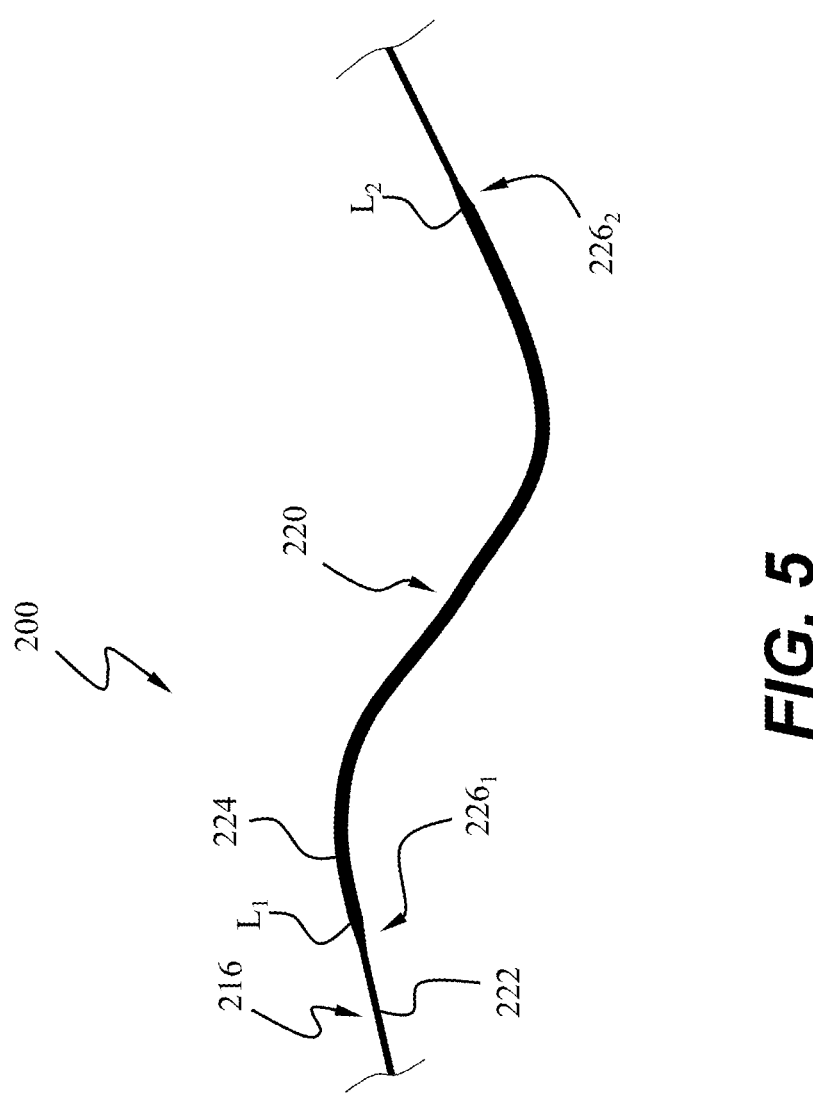
FIG. 5 is another exemplary suture assembly, in accordance with this disclosure.

Turning to FIG. 5, the wire portion 220 of suture assembly 200 is depicted in greater detail. More specifically, the wire portion 220 may include a second transition 226$_2$, the overall length, L, of the wire portion 224 extending between L$_1$ and L$_2$. The overall length, L, may be any suitable length to ensure that the wire portion 224 extends through biological tissue through which needle portion 214 has passed. For illustration purposes and with respect to a sternal closure procedure, the overall length, L, of the wire portion 224 may be in the range from about 3 inches to about 5 inches.

Figure 6A:
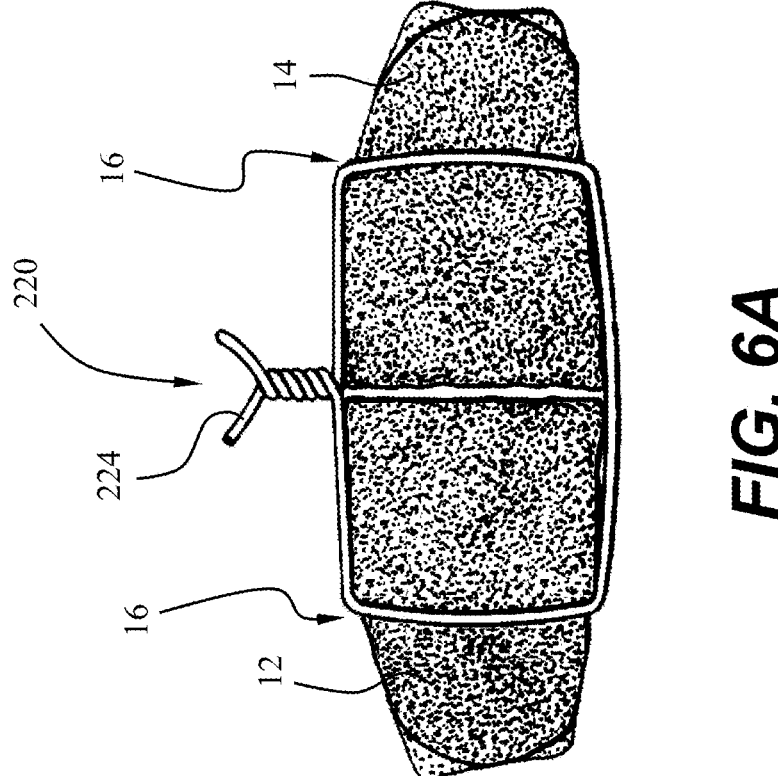
FIG. 6A depicts a section view of the partial sternum of FIG. 1, and the exemplary suture assembly of FIG. 4.

Turning to FIG. 6A, during a sternal closure procedure the two sternum portions 12, 14 are closed using wire portion 220 of the suture assembly 200 of FIG. 4. Once the needle portion 210 and a length of the wire portion 220, i.e., including wire portion 224, are passed through openings 16, the wire portion 220 may then be twisted to hold the sternum portions 12, 14 in place. The wire portion 220 may be disconnected from the needle portion 210 at a location proximal to the transition 216. Once disconnected the wire portion 220 may then be twisted to tighten the suture. Since the diameter of the wire portion 220 between the transitions 226$_1$, 226$_2$, e.g., wire portion 224, is greater than the diameter of the needle portion 210 and the diameter of a distal portion 222 or the wire 220, the wire portion 220 may reduce the space associated with the openings 16 and make better overall contact with the biological tissue about the openings 16, resulting in less bleeding. While discussed with respect to the wire portion 224 extending through the twisted portion of the suture, the wire portion 224 may minimally only extend through bottom openings 16B and along the bottom surface of sternum portions 12, 14, the transitions 226$_1$, 226$_2$ being located within the openings 16, for example. Alternatively, the wire portion 224 may extend completely through the openings 16, however end prior to the twisted portion. For example, the transitions 226$_1$, 226$_2$ may be positioned along a top surface of the sternum portions 12, 14. Wire portion 224 may be selected having a diameter that may be difficult to twist. In this case, the transitions 226$_1$, 226$_2$ may be located along the top surface of the sternum portions 12, 14 prior to the twist, the twist including wire portion 222 having a smaller diameter making the twisting of the wire easier. The location of the transitions 226$_1$, 226$_2$ may be visibly identifiable, e.g., through color coding as discussed immediately below, to allow a surgeon to more readily position the wire portion 220.

Figure 6C:
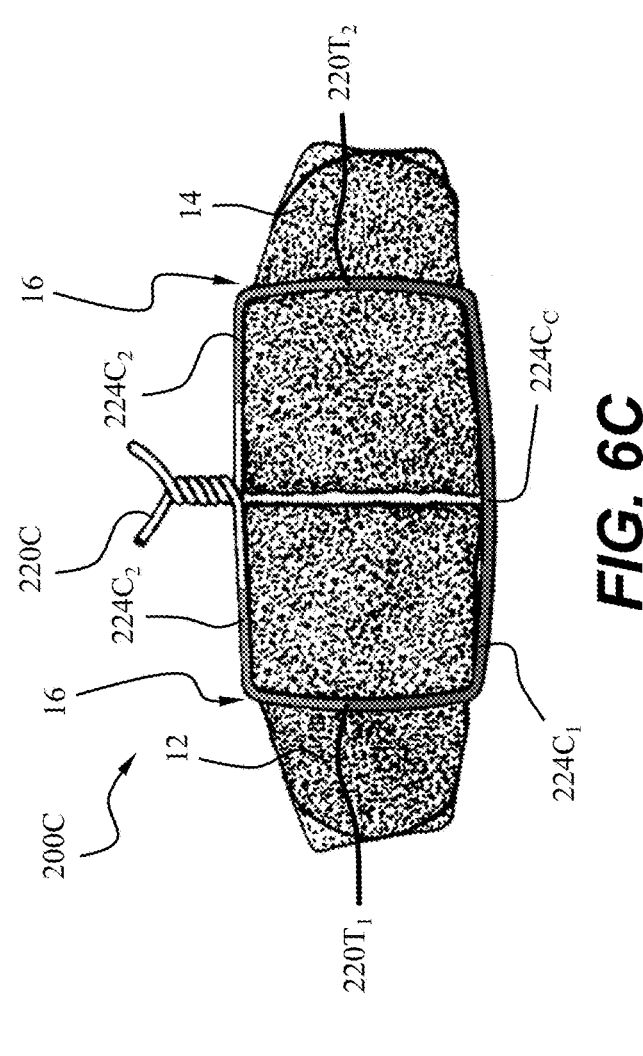
FIG. 6C is another exemplary suture assembly including visual elements.
Figure 6B:
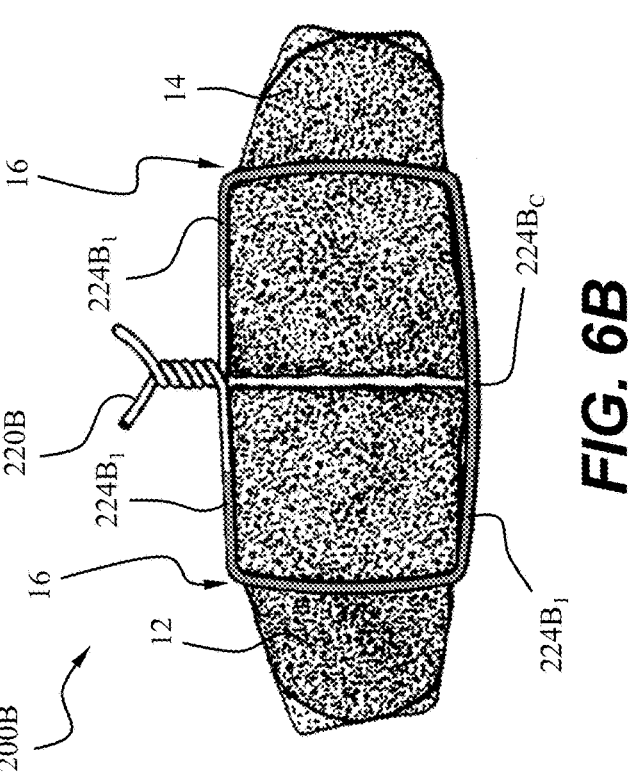
FIG. 6B is an exemplary suture assembly including visual elements.

Turning to FIG. 6B, another exemplary suture assembly 200B is depicted. Suture assembly 200B is similar to suture assembly 200, however, includes a colored wire portion 224B$_1$, shown in greyscale, as part of wire portion 220B. The selected color may be any suitable color that provides a surgeon with proper visualization, made from a biocompatible material. The colored wire portion 224B$_1$, for example, may be consistent with wire portion 224 having a diameter greater than an associated needle portion 210 of suture assembly 200B. While the colored wire portion 220B$_1$ is depicted as extending symmetrically about a center 220B$_C$ of wire portion 220B, the colored wire portion 224B$_1$ may be only exist at endpoints symmetrically located with respect to center 220B$_C$. In any case, the suture assembly 200B, through the use of one or more colored portions 220B$_1$, may provide a surgeon a visual indication that the wire portion 220B is central about sternum portions 12, 14, ensuring that the wire portion 224B extends through openings 16. The transitions 226B$_1$, 226B$_2$ of wire portion 220B may be adjacent to the corresponding ends of colored portion 224B$_1$, such that the wire portion 220B may have a diameter smaller than a diameter of colored portion 224B$_1$. The smaller respective diameter of the wire portion 220B may allow a surgeon to more easily twist the wire portion 220B, to tighten the suture. If the diameter of the wire portion 224B is more easily twisted then it may extend through the twisted portion of wire 220B and, accordingly, the colored wire portion 224B$_1$ may extend through the twisted portion, as well.

Turning to FIG. 6C, another exemplary suture assembly 200C is depicted. Suture assembly 200C may be similar to suture assembly 200, except includes multiple colored portions extending symmetrically about a center 220C$_C$ of wire portion 220C. One, some, or all the multiple colored portions may correspond to a wire portion 224C having a diameter greater than wire portion 220C adjacent to corresponding transitions 226C$_1$, 226C$_2$. For example, the wire portion 220C may include a first colored portion 224C$_1$, and two second colored portions 224C$_2$ located about the first colored portion 224C$_1$. The first colored portion 224C$_1$ may transition to the two second colored portions 224C$_2$ at corresponding color transition points 220T$_1$, 220T$_2$. The first and the second colors of the first colored portion 224C$_1$ and the second colored portion 224C$_2$, respectively, may be any suitable colors that provide a surgeon with proper visualization made from biocompatible material. As with the wire portion 220B, the transitions 226C$_1$, 226C$_2$ of wire portion 220C may be adjacent to the corresponding ends of colored portions 220C$_2$, such that the wire portion 220C may have a diameter smaller than a diameter of colored portions 220C$_1$, 220C$_2$. Alternatively, the transitions 226C$_1$, 226C$_2$ may correspond to the color transition points 220T$_1$, 220T$_2$, the diameter of colored portions 224C$_2$ being less than a diameter of colored portion 224C$_1$.

Figures 7, 8A, 8B:
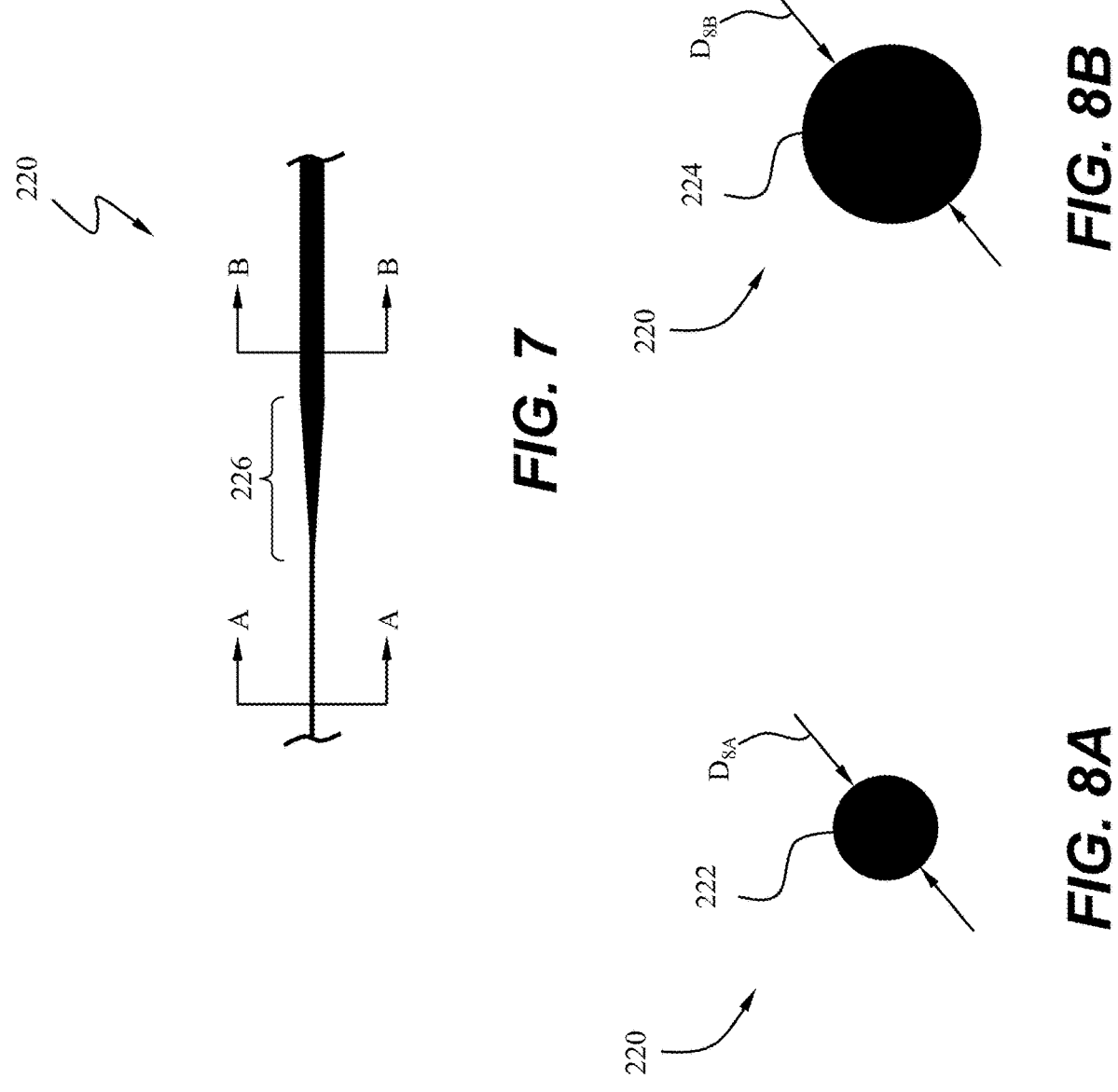
FIG. 7 is a more detailed depiction of a portion of an exemplary suture assembly, in accordance with this disclosure.
FIG. 8A depicts a section view of a portion of the exemplary suture assembly of FIG. 7 at a first location.
FIG. 8B depicts a section view of another portion of the exemplary suture assembly of FIG. 7 at a second location.

Turning to FIG. 7, the transition 226 of surgical suture assembly 200 is depicted in greater detail. The wire portion 220 may have a first diameter at section A and a second diameter at section B, section B being located along wire portion 224, the diameter of section B being greater to the diameter of section A. As should be readily understood, while the transition 226 is immediately being discussed, this discussion may apply to any other transition as part of any suture assembly described or contemplated herein. The transition 226 may be created in any suitable fashion. For example, the wire portion 220 may originally have a constant diameter along its entire length, a distal end of the wire portion 220 may be then milled to provide a desired transition 226. Alternatively, the wire portion 220 may include one or more individual wires, any number of individual wire including a transition 226. In other exemplary embodiments, the transition 226 may be formed through the addition of one or more wires. While the individual wire geometric cross-sections discussed below are depicted as circular, any suitable cross-sectional geometry may be used. Additionally, the wire portion 220 may include more than one cross-section such that a first geometric cross-section is located on a first side of the transition 226 and a second geometric cross-section is located on a second side of the transition 226. Alternatively, one or more of the individual wires may have a first geometric cross-section and the remaining individual wires may have a second geometric cross-section, or each of the individual wires may have any suitable geometric cross-section.

Figure 9A:
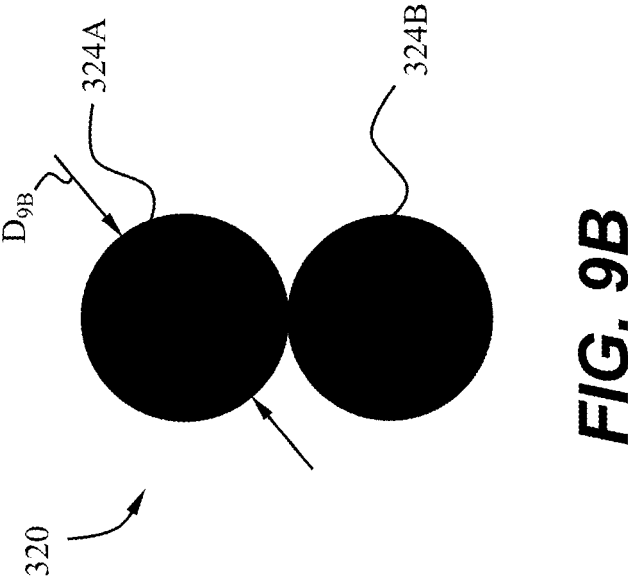
FIG. 9A depicts a section view of a portion of the exemplary suture assembly of FIG. 7 at a first location.
Figure 9B:
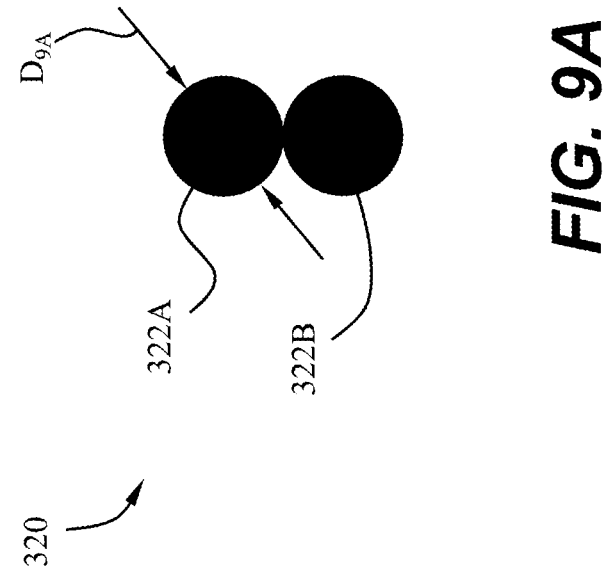
FIG. 9B depicts a section view of another portion of the exemplary suture assembly of FIG. 7 at a second location.

With continued reference to FIG. 7, turning to FIGS. 8A and 8B, the wire portion 220 may include wire portion 222 having a first diameter D$_{8A}$ at section A, as depicted in FIG. 8A, and wire portion 224 having a second diameter D$_{8B}$ at section B, as depicted in FIG. 8B, the second diameter D$_{8B}$ being larger than the first diameter $D_{8A}$. For illustration purposes, the ratio of any transition discussed herein, for example, the ratio of the second diameter $D_{8B}$ to the first diameter $D_{8A}$ may be in the range from about 1 to about 3. Alternatively, the wire portion 220 may include two or more individual wire portions, as depicted in FIGS. 9A-11B. Turning to FIGS. 9A and 9B, a wire portion 320 may include two wire portions 322A, 322B, each having a first diameter $D_{9A}$ at a distal end 322 of wire portion 320, as depicted in FIG. 9A, and each wire portion 324A, 324B having a second diameter $D_{9B}$ at the proximal end 324 of transition 326, diameter $D_{9B}$ being greater than diameter $D_{9A}$.

Figures 10A, 10B:
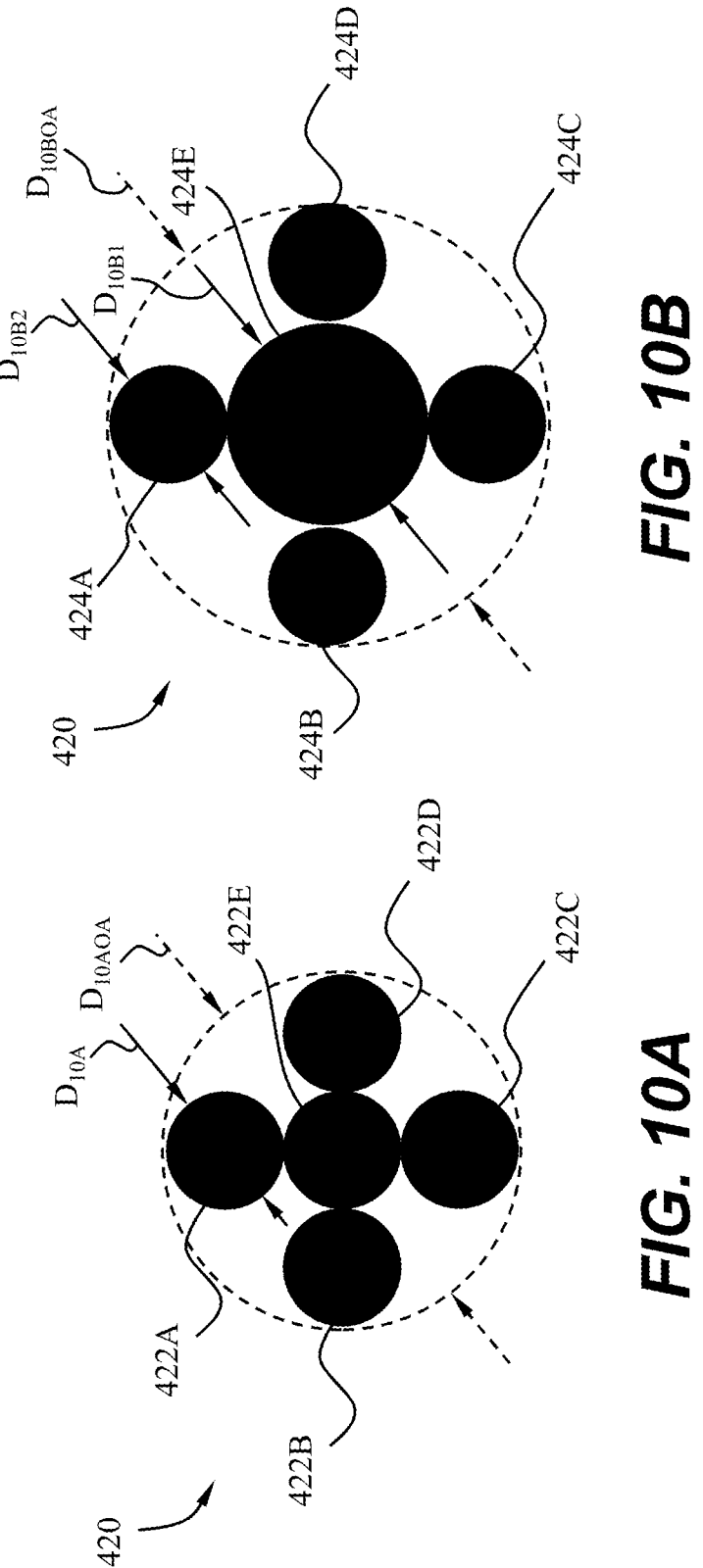
FIG. 10A depicts a section view of a portion of the exemplary suture assembly of FIG. 7 at a first location.
FIG. 10B depicts a section view of another portion of the exemplary suture assembly of FIG. 7 at a second location.

Some embodiments of the wire portion, e.g., wire portion 220 or similar, may include a plurality of individual wires or monofilaments, one or more of the plurality of individual wires may have a first diameter and a second diameter along its length. Accordingly, the overall diameter of the wire embodiment may include a transition between the portions of the one or more of the plurality of wires between the first diameter and the second diameter. Turning to FIGS. 10A and 10B, an example of one such embodiment includes a wire portion 420 having a plurality of individual wire portions of a first diameter $D10_A$, i.e., wire portions 422A through 422E, at a distal end 422 of the wire portion 420, corresponding to section A of FIG. 7, the overall diameter being $D10_{AOA}$. Additionally, at a proximal end of transition 426, the wire portion 424 includes wire portions 424A through 424E, corresponding to section B of FIG. 7, the overall diameter being $D10_{BOA}$. At least one of the plurality of individual wire portions includes a first diameter Thom, while each of the remaining ones of the plurality of individual wire portions includes a second diameter $D10_{B2}$, diameter Diose being greater than diameter $D_{10B2}$. With diameter $D_{10B2}$ being the same as diameter $D_{10A}$ and wire portion 424E having a diameter $D_{10B1}$ that is larger than diameter $D_{10A}$, the overall diameter $D_{10BOA}$ is greater than the overall diameter $D_{10AOA}$. Although depicted as having the same diameter, each of the wire portions 424A-424D may have a diameter that is equal to or different than diameter $D_{10A}$.

Figures 11A, 11B:
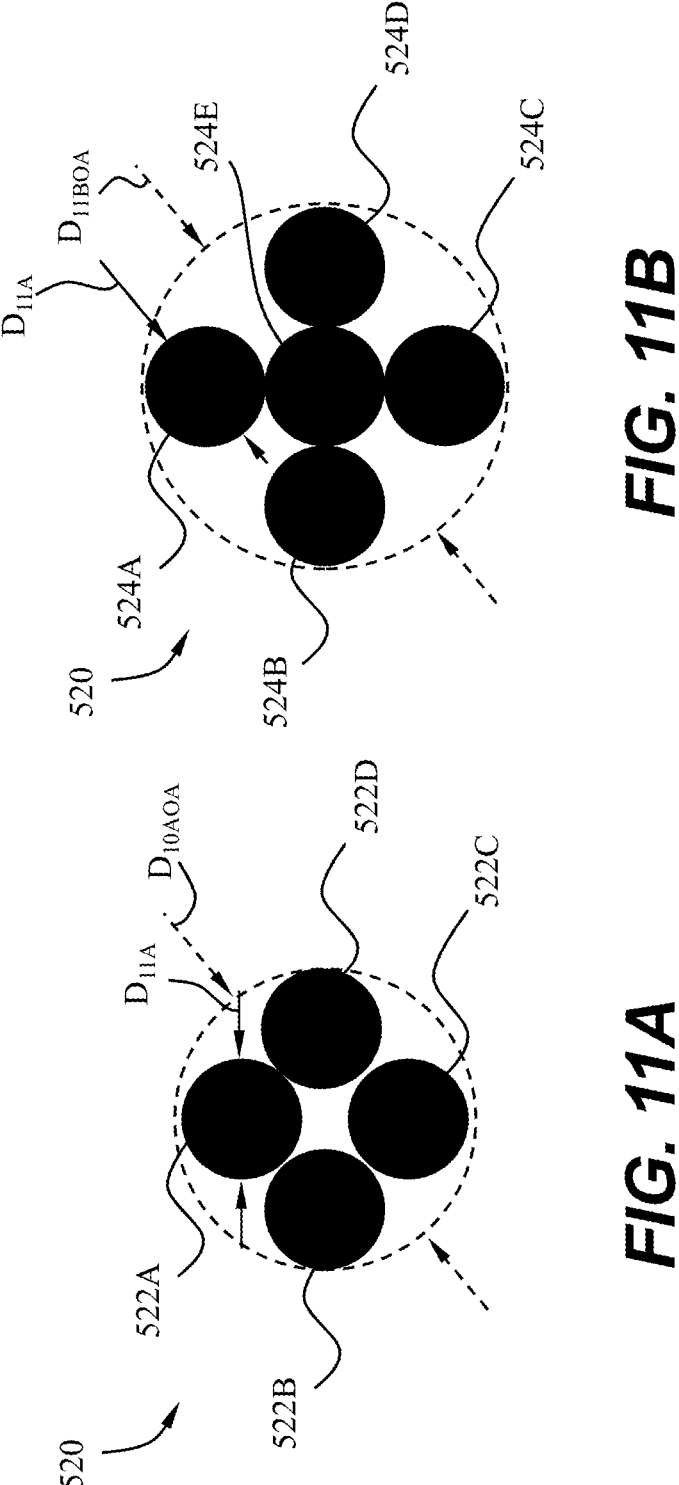
FIG. 11A depicts a section view of a portion of the exemplary suture assembly of FIG. 7 at a first location.
FIG. 11B depicts a section view of another portion of the exemplary suture assembly of FIG. 7 at a second location.

Some embodiments of the wire portion may include a first plurality of individual wires on one side of a transition and a second plurality of individual wires on a second side of the transition, a total number of the second plurality of wires being greater than a total number of the first plurality of wires. Accordingly, the overall diameter of the wire embodiment may include a transition between the portions of the one or more of the plurality of wires between the first diameter and the second diameter. Turning to FIGS. 11A and 11B, an example of one such embodiment includes a wire portion 520 having a plurality of individual wire portions of a first diameter $D11_A$, i.e., wire portions 522A through 522D, at a distal end 522 of the wire portion 520, corresponding to section A of FIG. 7, the overall diameter being $11_{AOA}$. Additionally, at a proximal end 524 of transition 526, the wire portion 520 includes wire portions 524A through 524E, corresponding to section B of FIG. 7, the overall diameter being $11_{BOA}$. Each of the first plurality of wire portions 522 includes a first diameter $D_{11A}$, while each of the second plurality of wire portions 524 includes a second diameter Dim the diameter $D_{11A}$ being substantially the same as diameter $D_{11B}$, however since there are a greater number of wires in the second plurality of wires as compared to the first plurality of wires, the overall diameter $D_{11BOA}$ is greater than the overall diameter $D_{11AOA}$. Although depicted as having the same diameter, each of the wire portions 524A-524D may have a diameter that is equal to or different than diameter $D_{11A}$.

Embodiments described herein including a plurality of wires, for example, those embodiments of FIGS. 9-11, may include an outer covering of a biocompatible material to hold portions of the plurality of wires in position relative to each other. Such coverings may be configured to shrink upon application of heat, and may include biocompatible epoxy to hold the covering in place. Alternatively, the plurality of wire portions may be held fast to each other without a covering present, but through the use of a biocompatible epoxy, the epoxy smoothed to provide a fillet between adjacent wire portions. Preferably, the biocompatible epoxy described herein is a flexible epoxy allowing for easy bending of the multiple wire portions. The outer covering may define a portion of a desired diameter as part of the wire portion, as described herein. The covering may be compressible and/or elastic to allow for better biological tissue contact, while mitigating passage of blood.

It should be understood, features of any one of the above-described embodiments described herein may be applied to any other of the above-described embodiments, as appropriate. The surgical suture assemblies described herein may be made from any suitable biocompatible material, including but not limited to metals, metal alloys (e.g., stainless steel or nitinol) and polymers (e.g., polycarbonate or Teflon™), and may be formed using any appropriate process, such as the use of a lathe and grinding, cutting, sanding, knurling, drilling, deformation, facing, turning, with appropriate tools or molding (e.g., injection molding).

The invention claimed is:

1. An assembly, comprising:
    a needle portion having a maximum diameter, a tapered distal portion ending in a distal tip, and a proximal end; and
    a wire portion coupled to the proximal end of the needle portion, the wire portion including a wire, the wire having a distal end, a proximal end, a transition portion, a distal portion extending from the distal end of the wire to a distal end of the transition portion, and a proximal portion extending from a proximal end of the transition portion to the proximal end of the wire, a first diameter at a first location along the distal portion of the wire and a second diameter at a second location along the proximal portion of the wire, the second diameter being greater than the first diameter,
    the wire formed from metal, the wire having a smooth outer surface and a solid cross section extending along the entire length of the wire, the solid cross section of the wire being a solid circular cross section along the distal and proximal portions of the wire, and
    an overall diameter of the wire portion at the second location of the wire being greater than both an overall diameter of the wire portion at the first location of the wire and the maximum diameter of the needle portion.

2. The assembly of claim 1, wherein the distal portion of the wire adjacent the distal end of the transition portion has a diameter equal to the first diameter of the wire and the proximal portion of the wire adjacent the proximal end of the transition portion has a diameter equal to the second diameter of the wire, and the transition portion includes a diameter that transitions over its length from the first diameter of the distal portion of the wire to the second diameter of the proximal portion of the wire.

3. The assembly of claim 1, wherein the distal portion of the wire includes a diameter equal to the first diameter of the wire along the entire length of the distal portion of the wire, and the proximal portion of the wire includes a diameter equal to the second diameter of the wire along the entire length of the proximal portion of the wire, and the transition portion includes a diameter that transitions over its length from the first diameter of the distal portion of the wire to the second diameter of the proximal portion of the wire.

4. A surgical suture assembly, comprising:

a needle portion having a maximum diameter; and a wire portion coupled to the needle portion, the wire portion including a wire, the wire having a first end, a second end, a transition portion, a first portion extending from the first end of the wire to a distal end of the transition portion and a second portion extending from a proximal end of the transition portion to the second end of the wire, a first location along the first wire portion having a first diameter and a second location along the second wire portion having a second diameter, the second diameter being greater than the first diameter, the transition portion located between the first location and the second location along the wire, the wire formed from a single material, the wire having a smooth outer surface and a solid cross section extending at least from the first location, through the transition portion, to the second location, the solid cross section being a solid circular cross section at the first location and the second location, and an overall diameter of the wire portion at the second location of the wire being greater than both an overall diameter of the wire portion at the first location of the wire and the maximum diameter of the needle portion.

5. The surgical suture assembly of claim 4, wherein the wire is a first wire, the wire portion further including a second wire, the second wire having a length extending at least from the first location of the first wire to the second location of the first wire, the second wire having a constant diameter along its length.

6. The surgical suture assembly of claim 5, wherein the second wire is a first of a plurality of second wires, each of the plurality of second wires having a length extending at least from the first location of the first wire to the second location of the first wire, each of the plurality of second wires having a constant diameter along its respective length.

7. The surgical suture assembly of claim 4, wherein the wire is a first wire, the wire portion further including a second wire, the second wire having a length extending at least from the first location of the first wire to the second location of the first wire, the second wire having a first diameter at a first location of the second wire, a second diameter at a second location of the second wire, and a transition portion between the first location and the second location of the second wire, the second diameter of the second wire being greater than the first diameter of the second wire.

8. The surgical assembly of claim 7, wherein the first location of the first wire and the first location of the second wire are at a first location of the wire portion, and the second location of the first wire and the second location of the second wire are at a second location of the wire portion.

9. A surgical suture assembly, comprising:

a needle portion having a maximum diameter, a tapered distal portion ending in a distal tip, and a proximal end; and a wire portion coupled to the proximal end of the needle portion, the wire portion including a wire, the wire having a distal end, a transition portion, a distal portion extending from the distal end of the wire to a distal end of the transition portion, and a proximal portion extending proximally from a proximal end of the transition portion, a first diameter at a first location along the distal portion of the wire and a second diameter at a second location along the proximal portion of the wire, the wire formed from metal, the wire having a smooth outer surface and a solid cross section extending along the entire length of the wire, the solid cross section of the wire being a solid circular cross section at least at a location where the distal end of the transition portion meets the distal portion of the wire, and an overall diameter of the wire portion at the second location of the wire being greater than both an overall diameter of the wire portion at the first location of the wire and the maximum diameter of the needle portion.

10. The assembly of claim 9, wherein the distal tip of the needle portion includes a sharpened tip.

11. The assembly of claim 9, wherein the needle portion is substantially straight.

12. The assembly of claim 9, wherein the needle portion includes a curved portion.

13. The assembly of claim 9, wherein the ratio of the second diameter of the wire to the first diameter of the wire is in a range from about 1 to about 3.

14. The assembly of claim 9, wherein the wire is a first wire, the wire portion further including a second wire extending from the first location to the second location of the first wire.

15. The assembly of claim 14, wherein the wire portion includes an outer covering of biocompatible material.

16. The assembly of claim 14, wherein the second wire includes a constant diameter along its entire length.

17. The assembly of claim 14, wherein the second wire is a first of a plurality of second wires, the first of the plurality of second wires including a diameter that is different from a diameter of each of the remaining ones of the plurality of second wires.

18. The assembly of claim 14, wherein the second wire is a first of a plurality of second wires, each of the plurality of second wires having a diameter that is different from a diameter of each of the remaining ones of the plurality of second wires.

19. The assembly of claim 14, wherein the second wire is a first of a plurality of second wires, a first group of the plurality of second wires having a first diameter and a second group of the plurality of second wires having a second diameter, the first diameter of the first group of the plurality of second wires being different than the second diameter of the second group of the plurality of second wires.

20. The assembly of claim 14, wherein the second wire is a first of a plurality of second wires, a first number of the plurality of second wires located at a first distance from the proximal end of the needle portion, and a second number of the plurality of second wires located at a second distance from the proximal end of the needle portion.

21. The assembly of claim 14, wherein the second wire is a first of a plurality of second wires, a first number of the plurality of second wires located at the first location of the first wire and a second number of the plurality of second wires located at the second location of the first wire.

22. The assembly of claim 9, wherein the overall diameter of the wire portion increases along a length of the transition portion from the overall diameter of the wire portion at the first location of the wire to the overall diameter of the wire portion at the second location of the wire.

* * * * *